United States Patent [19]

Barlow et al.

[11] Patent Number: 4,597,395

[45] Date of Patent: Jul. 1, 1986

[54] ANKLE SUPPORT INCLUDING A HEEL LOCK AND A CROSSOVER STRAP

[75] Inventors: Carl S. Barlow; Alfred G. Jacobson, both of Sandpoint, Id.

[73] Assignee: Barlow, Inc., Sandpoint, Id.

[21] Appl. No.: 768,704

[22] Filed: Aug. 23, 1985

[51] Int. Cl.⁴ ............................................. A61F 3/00
[52] U.S. Cl. .................................. 128/80 H; 128/166
[58] Field of Search .................. 128/166, 166.5, 165, 128/169, 155, 80 R, 80 H, 80 D, 82

[56] References Cited

U.S. PATENT DOCUMENTS

| | | | |
|---|---|---|---|
| 991,831 | 5/1911 | Collis | 128/166 |
| 1,374,669 | 4/1921 | McClellan | 128/166 |
| 2,446,902 | 8/1948 | Brand | 128/166 |
| 3,073,305 | 1/1963 | Biggs, Jr. et al. | 128/166 |
| 3,490,450 | 1/1970 | Gardner | 128/166 |
| 3,699,959 | 10/1972 | Garrahan et al. | 128/166 |
| 3,777,751 | 12/1973 | Wise | 128/166 |
| 3,934,583 | 1/1976 | Hollingshead et al. | 128/165 |
| 4,133,311 | 1/1979 | Karczewski | 128/166 |
| 4,166,460 | 9/1979 | Applegate | 128/80 H |
| 4,313,433 | 2/1982 | Cramer | 128/166 X |
| 4,367,733 | 1/1983 | Stromgren | 128/166 |
| 4,392,487 | 7/1983 | Selner et al. | 128/166 X |
| 4,495,942 | 1/1985 | Palumbo | 128/80 H |

FOREIGN PATENT DOCUMENTS 719993 11/1943 Fed. Rep. of Germany ...... 128/166

Primary Examiner—Clifford D. Crowder
Attorney, Agent, or Firm—Wells, St. John & Roberts

[57] ABSTRACT

An ankle support assists in providing comfort and support to the tissues of the human ankle. The support may include inter-connected dorsal, plantar and heel straps forming a heel lock that can be fitted to the heel area of the foot. A crossover strap is connected to the heel strap and includes free ends that can be extended from behind the heel and be releasably secured to the heel lock forward of the ankle. Fastener members are provided on the heel lock and at ends of the crossover strap to secure the crossover strap in its operative position. The fastener members are attached to ends of the straps comprising the heel lock and crossover strap to minimize the overall thickness of the connected fastener members when they are secured together.

17 Claims, 9 Drawing Figures

U.S. Patent  Jul. 1, 1986  Sheet 1 of 2  4,597,395
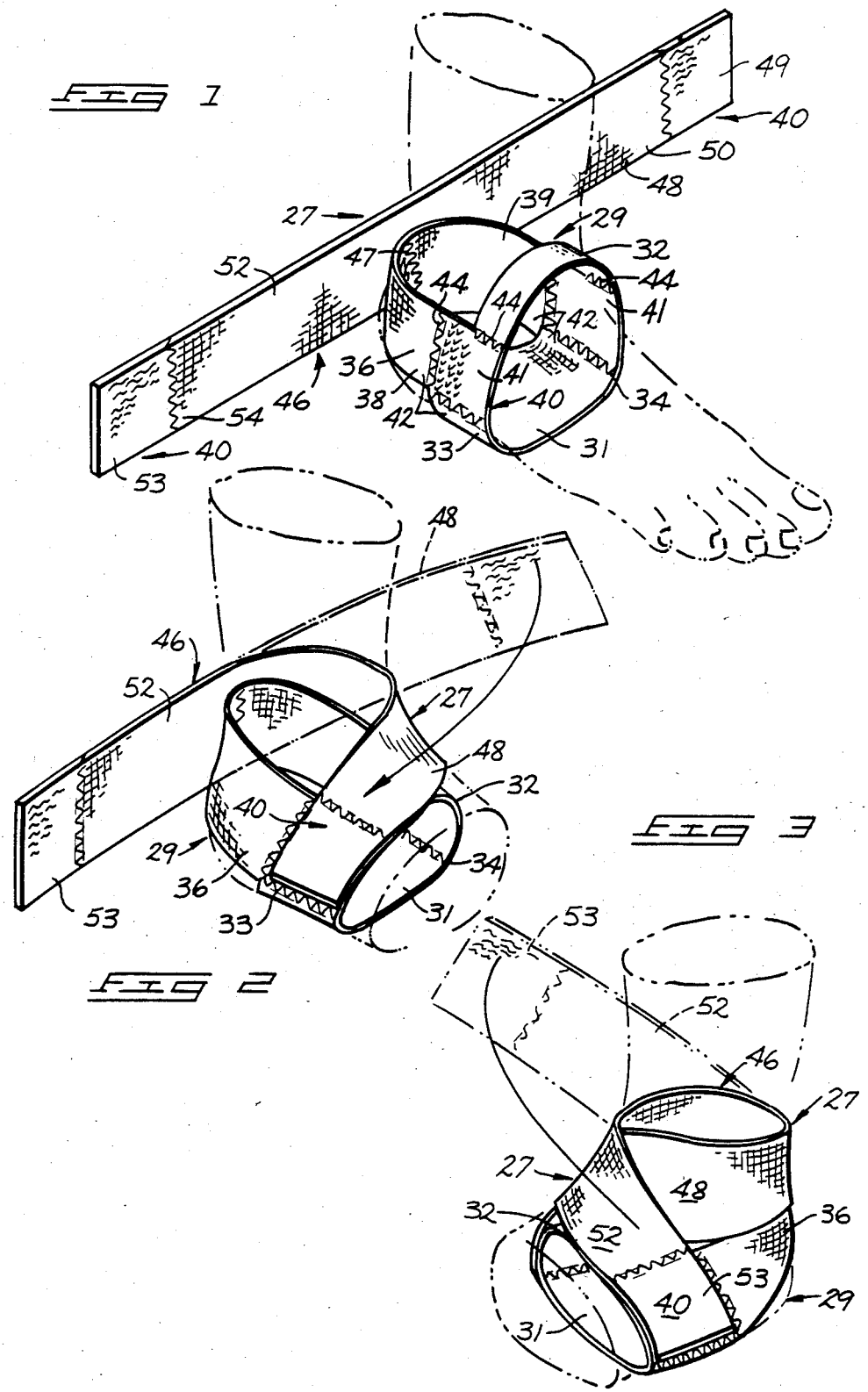

U.S. Patent   Jul. 1, 1986   Sheet 2 of 2   4,597,395
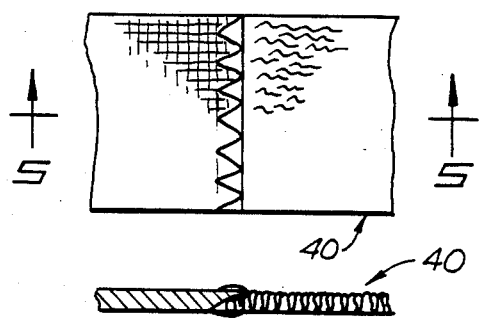
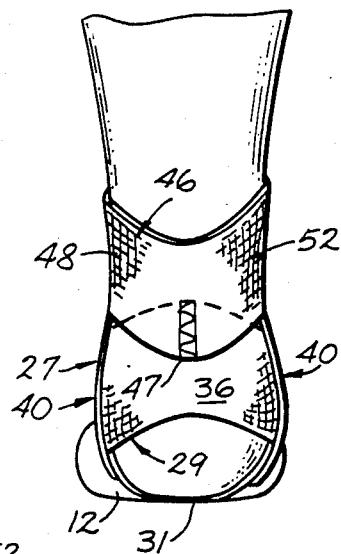
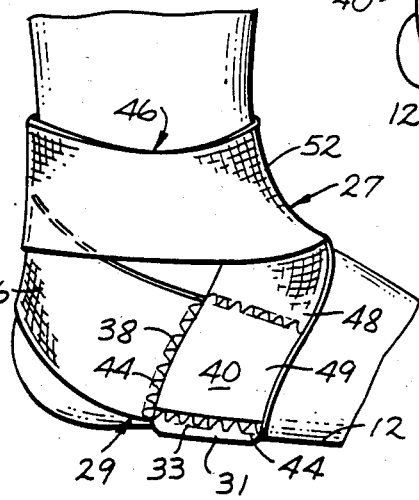
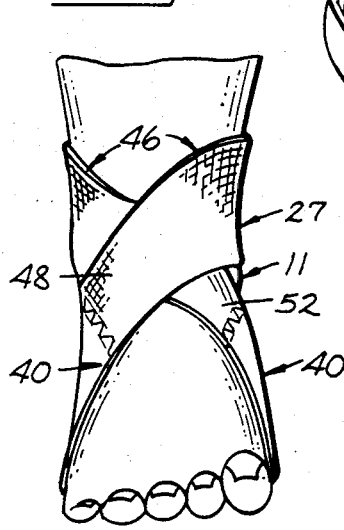
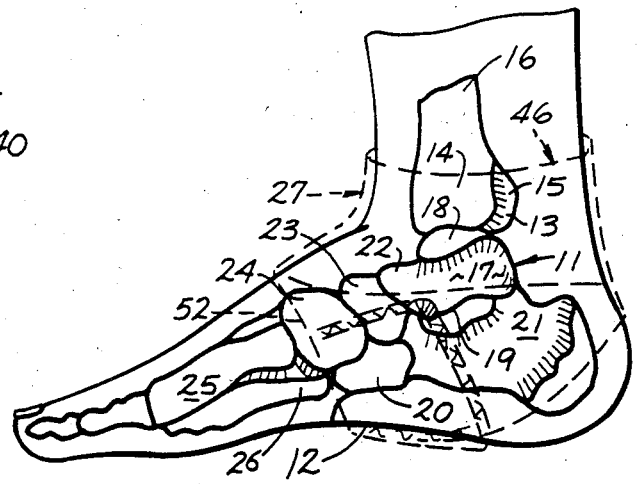

ANKLE SUPPORT INCLUDING A HEEL LOCK AND A CROSSOVER STRAP

FIELD OF THE INVENTION

The present invention relates to supplementary support for the ankle and consequent prevention of trauma to the ankle from malpositioning of the foot in relation to the lower leg.

BACKGROUND OF THE INVENTION

People involved in running sports or activities involving quick foot movement should have their ankles taped or wrapped with elastic bandages before any strenuous activities. Properly applied tape or elastic bandages will add support to the ankle area and prevent injury and secure previously injured tissues in place.

Many individuals experience difficulty from their ankles but do not have adequate training or assistance to properly wrap the weak ankles for greatest support and protection. This is most often true of athletes and older individuals. The elderly, in addition to ankle support problems, may also have other infirmaties (such as rheumatism or arthritis) that severely limit their physical abilities to apply the usual ankle wrap. Even so, it remains desirable to properly tape or bandage weak or injured ankles to avoid injury and provide the comfort that added support brings.

Conventional ankle wrapping operations are fairly complex operations, best left to trained personnel when existing tape or elastic bandages are used. Proper training is not typically available to the individual. Even trained athletes are not often trained to properly apply tape or elastic wrap to the correct areas of the ankle for best support and protection.

There is also the possibility that incorrect tension can be applied even though the tape or wrap is properly positioned. Too much tension will cause discomfort, cut off circulation, and inhibit free dorsiflexion and plantar flexion of the foot. Too little tension will defeat the purpose of the wrap to strengthen the joint against unwanted inversion and eversion of the foot.

Ankle wrapping is a slow and tedious process. With athletes, wrapping takes up valuable practice or competition time and valuable time of the trained attendant. Because of the time loss and tedious nature of the wrapping process, many forego wrapping or taping and simply risk the ankle injury.

The relatively high cost of tape is another consideration that causes many to forego ankle wrapping. Most tape can be applied only once, and when removed, cannot be adequately used again. Elastic wrap can be used again but requires extra care in application due its elastic nature and the tendency to cut off circulation to the extremities of the foot.

U.S. Pat. No. 4,367,733 to Stromgren represents a partial recognition of the above problems. Stromgren discloses an ankle support that makes use of an elastic stocking member having one end of an elongated elastic strap secured thereto. The open toed stocking member can be slipped over the foot adjacent the ankle area. The elongated strap is then wrapped about the ankle in a specified procedure, similar to that used with conventional elastic wrap. The wrapping procedure requires an adequate understanding of the proper placement for wraps to secure the ankle in a "double heel lock" as desired with conventional wrapping.

Stromgren provides securing patches by which sections of the elastic bandage are held in position in relation to one another. The securing patches are placed across the strap. The patches are spaced apart so that they will come together once the elastic strap has been properly wrapped about the foot and ankle. The connecting patches are intended to serve as guides for indicating proper wrapping procedures to the user. An elastic bandage, however, can be made to stretch substantially more than its ordinary length. The bandage could therefore be stretched to misposition the patches and consquently misguide the trainer or wearer as to proper application and tension.

Stromgren illustrates the need commonly experienced by athletes or others who attempt to wrap or tape their own ankles. It effectively anchors one end of the elongated strap and, in that regard, assists in the wrapping procedure. However, a need remains for a reusable ankle support that can be easily, quickly, and effectively applied without risking improper positioning of the various desired support elements and that can be applied in a compact manner such that the wrap does not interfere with shoes or other footwear.

An earlier attempt to fulfill the above needs is found in U.S. Pat. No. 2,446,902 to Jane Brand. Brand attaches two elastic straps to a larger single elastic strap, forming a somewhat tubular shaped support. The support can be positioned over the foot and heel area with the two smaller strap sections extending about the back or posterior surface of the heel and the plantar surface of the foot. The larger strap extends over the dorsal surface of the foot in the area of the ankle. The straps, being fixed to one another, limit use of the support to a particular size.

U.S. Pat. No. 3,699,959 to Garrahan discloses an ankle wrap making use of a heel lock formed of an elastic strap. An elongated free end of the strap extends from the heel lock to be wrapped in a substantially conventional manner about the wearer's ankle.

U.S. Pat. No. 3,777,751 to Wise discloses an ankle support strap using a loop at one end as a heel lock. The loop secures one end of the strap to the foot. The free strap end is then used to wrap the ankle area.

U.S. Pat. No. 1,374,669 to McClellan discloses a lace or buckle type support that can be strapped into position on the wearer's foot. Tension is adjusted by a buckle arrangement.

U.S. Pat. No. 991,831 to Collis discloses a stocking type ankle support made up of interconnected sections of elastic and nonelastic materials. This support performs a function somewhat similar to existing forms of support stockings.

A somewhat similar support arrangement is illustrated in U.S. Pat. No. 3,934,583 to Hollingshead et al. The Hollingsead device includes a stocking arrangement that is folded from a flat pattern configuration. When folded, the flat pattern resembles the Collis support stocking.

U.S. Pat. No. 4,166,460 to Applegate discloses an ankle protector with a stocking used to support attached lengths of wrap that can be wound about the wearer's ankle and lower leg to secure substantially rigid brace members in position relative to a heel cup.

Of the above references, none show or suggest a complete, adequate solution to the problem in providing an easily positioned, reusable, compact, and comfortable support for a wearer's foot and ankle area that can be quickly applied by the wearer without requiring additional help and that will not add significant bulk to specific areas of the wearer's ankle.

BRIEF DESCRIPTION OF THE DRAWINGS

A preferred form of the invention is illustrated in the accompanying drawings, in which:

FIG. 1 is a graphic view of the present support secured to a wearer's ankle which is shown by dashed lines;

FIG. 2 is an operational view from the lateral side of a wearer's foot showing the initial steps involved in applying the present support to the foot;

FIG. 3 is an operational view of a foot from the medial side illustrating completion of the application procedure for the present support;

FIG. 4 is a detail veiw of a typical joint between a fastener member and strap of the present invention;

FIG. 5 is a sectional view taken line 5—5 in FIG. 4;

FIG. 6 is a frontal view of a foot with the present support mounted thereto;

FIG. 7 is a back side view of the foot and support shown in FIG. 6;

FIG. 8 is a medial side view illustrating the general anatomy of a foot and ankle area, the present support being shown by dotted lines thereon; and FIG. 9 is a lateral side view of the foot and support shown in FIGS. 6 and 7.

DETAILED DESCRIPTION OF THE PREFERRED EMBODIMENT

In compliance with the constitutional purpose of the Patent Laws "to promote the progress of science and useful arts" (Article 1, Section 8), applicants submit the following disclosure of the invention.

FIG. 8 of the drawings is generally descriptive of a human foot 10 and ankle area or tarsus 11. The present support is intended to be fitted over the foot in the area of the ankle or tarsus 11 for providing support and protection of underlying muscles and tendons and other tissues in the tarsal area. FIG. 8 also diagrammatically illustrates the skeletal features of the human foot from the medial or inside surface.

The area of the foot between the ankle and toes may be defined as the arch or instep area and is indicated at 12. The upward facing surface of the instep area is termed the "dorsal" surface while the bottom surface of the foot is referred to as the plantar surface or sole.

In terms of skeletal structure, the upper end of the ankle joint is made up of the two lower leg bones, the tibia 16 and the fibula 15. FIG. 8 illustrates the lateral malleolus 13 at the distal end of the fibula 15 and the medial malleolus 14 at the distal end of the tibia 16. The lateral and medial malleolus 13, 14 form the bony protrusions recognized commonly as the "ankle bones".

The downward facing or inferior surfaces of the tibia 16 and fibula 15 articulate with the talus 17 along its superior articular surfaces 18. The talus is the first of the seven bones of the ankle or tarsus 11. Inferior articular surfaces 19 of the talus 17 articulate with the calcaneum 21 or heel bone. The calcaneum 21 defines the shape of the heel and is the second bone of the tarsus 11.

An anterior surface 22 of the talus 17 articulates with the navicular 23, the third bone of the seven tarsal bones. The navicular 23 articulates with the cuboid 20, the fourth bone of the tarsus, and the three cuneformes 24; thus completing the remainder of the seven bones of the tarsus.

The cuneforms 24 extend across the width of the foot and articulate with the navicular 23 and cuboid 20. Anterior ends of the cuneforms 24 and cuboid 20 articulate with the five metatarsals 25. Each of the metatarsals 25 leads forwardly to an individual toe. Reference numeral 26 generally indicates the area of articulation between the tarsus 11 and the posterior ends of the metatarsals 25.

Given the above anatomical features, an adequate understanding may now be had regarding the particular placement and application of the present support.

The support embodying a preferred form of the present invention is generally indicated at 27 in the drawings. The support 27 is intended for use in encircling and compressing areas of the foot and lower leg in the vicinity of the tarsus 11. The elastic suppport constricts about engaged areas in order to supplement and strengthen underlying muscle and ligament tissues.

The present support 27 is easily secured to the wearer's foot by means of a heel lock 29. The heel lock 29 is mountable to the heel with a plantar strap 31 provided thereon extending laterally across the plantar surface of the foot along the instep just forward of the calcaneum 21. The plantar strap extends laterally between a lateral strap end 33 and a medial strap end 34. The lateral strap end is intended to project upwardly along the lateral surface of the foot while the medial end extends upwardly along the medial foot surface.

A dorsal strap 32 is also provided, extending opposite from the plantar strap and forming an open loop therewith. The dorsal strap is provided to hold the remainder of the heel lock 29 in place on the foot to ease attachment of the remainder of the support. The strap 32 is received over the dorsal surfaces of the foot as shown in FIG. 1.

The heel lock 29 also includes a heel strap 36. The heel strap 36 may extend substantially horizontally in a horseshoe configuration to embrace the Achilles tendon area of the foot. It extends forwardly from the Achilles tendon area along opposite lateral and medial sides of the foot to a lateral end 38 on the lateral foot surface and a medial end 39 along the medial foot surface. The length of the heel strap is sufficient to allow positioning of the ends 38 and 39 forwardly of the lateral and medial malleolus 13, 14.

A fastener means generally shown at 40 includes first fastener members 41 for securing the heel, plantar, and dorsal strap ends together in the configuration shown in the drawings. Specifically, the first fastener members 41 may be formed of a fabric fastener material such as currently sold under the trademark "Velcro" and shaped in polygonal configurations. Each of the first fastener members 41 therefore includes peripheral joined edges 42. Appropriate sections of the fastener edges 42 may be attached by securing devices such as stitching 44 to the lateral and medial ends of the plantar strap 31, the heel strap 36, and similar ends of the dorsal strap 32 as shown in FIG. 1.

Adjacent edges 42 of each member 41 may be substantially perpendicular to angularly orient the heel and plantar straps substantially perpendicularly as shown by FIGS. 1 and 9. The two straps, interconnected by the first fastener members 41, thereby form a pocket into which the wearer's heel may be freely received. The dorsal strap 32 serves to hold the straps 31, 36 in place on the foot, with the rearward or posterior external surface of the wearer's heel projecting between edges of the heel and plantar straps as shown in FIGS. 7 and 9.

It is noted that the plantar, dorsal and heel straps 31, 32 and 36 can be formed of elastic strap material. For straps 31 and 36, conventional 1½" or 2" wide elastic strap can be used for this purpose. The dorsal strap can be narrower. All straps may extend sufficiently to enable use of the present support through a relatively wide variety of foot sizes.

It should also be noted that the first fastener members 41 are connected to ends of the adjacent straps and do not overlap the strap materials. FIGS. 4 and 5 illustrate a typical interconnection between a fastener member and any one of the straps used with the present invention. This form of connection is important since it is desirable not to add bulk by overlapping or "stacking" several layers of material one on another.

Another important feature of the present support 27 is a crossover strap 46. The crossover strap 46 is provided on the heel lock and is selectively extendable over the dorsal surface of the foot and around the ankle area to secure the heel lock in position and to provide compression and support of underlying tissues. The crossover strap 46 is preferably elongated and elastic. It is preferably secured at a location approximately midway along its length to an area of the heel strap at the approximate center of the heel strap length. FIG. 7 shows the interconnection between the crossover strap 46 and heel strap 36. It may be formed by a line of appropriate stitching 47 as indicated in FIG. 7 that is substantially perpendicular to the heel and crossover strap lengths.

The relationship of the heel strap and crossover strap is significant. It is noted in FIGS. 7 and 9 that the straps overlap. That is, the width dimension of the heel strap is partially overlapped by the width dimension of the crossover strap with the crossover strap extending partially above the heel strap. With straps having common width dimensions of between 1½" and 2", this overlap dimension may be approximately 1". There is a particular reason for the overlap beyond selective positioning of the crossover strap elevationally in relation to the foot. If the two straps were to be connected such that their longitudinal side edges matched (the width of the heel strap and crossover strap completely overlapping) the lower edge of the heel strap would curl upwardly due to tension applied by the crossover strap when mounted to the foot. However, with the arrangement shown, the support can be secured to the user's foot with the strap surfaces lying in flush surface to surface engagement with the adjacent engaged areas of the heel and Achilles tendon area.

The crossover strap 46, when connected as shown in FIG. 1 to the heel strap 36, extends to substantially equal distances to opposite sides of the heel lock. The strap 46 is thereby divided into a medial crossover strap section 48 extending to a second fastener member 49 at a free end 50 thereof. The crossover strap 46 also includes a lateral strap section 52 extending to a second fastener member 53 at a free lateral strap section end 54. It is noted that the strap sections 52 terminate at ends 50, 54 and that the second fasteners 53 extend therefrom. The same form of connection is made between edges of the fastener members 49, 53 and strap ends 50, 54 as described above and shown in FIGS. 4 and 5. The thickness of the strap is therefore not added to the overall thickness dimension of the second fastener members. This facilitates a minimal thickness dimension when the second fastener members are secured to the first fastener members 41.

The individual sections of the crossover strap are of sufficient length to extend forwardly around the ankle area of the foot and over the dorsal surface thereof to the opposite sides from which they originate. In other words, the lateral strap section can be extended forwardly over the lateral malleolus, laterally or transversely across the dorsal surface of the foot to become attached by its second fastener member to the medial first fastener member. Likewise, the medial strap section can be extended forwardly over the medial malleolus, across the dorsal surface of the foot forward of the ankle to be attached on the lateral foot surface at the first fastener member thereon.

The following process may be followed when mounting the present support to a foot.

The first procedure involved in mounting the present support to a foot is slipping the loop formed by the dorsal strap 32 and the plantar strap 31 over the foot. The heel strap 36 can then be secured in position as shown in FIG. 1. The heel strap is positioned to extend around the heel along the Achilles tendon area thereof. Care is taken to substantially center the heel strap on the foot so the first fastener members extend forwardly from the heel by equal distances on opposite sides of the foot.

Next, with the dorsal strap holding the plantar and heel straps in position, the user grasps one of the sections of the crossover strap 46. This section is pulled forwardly to cover the adjacent malleolus of the ankle. It is then crossed over the dorsal surface of the foot and fastened, using the second fastening member thereon, to the first fastener member on the opposite side of the foot. More specifically, and using the lateral strap, for example, the free end of the lateral strap section may be pulled forwardly over the lateral malleolus, across the dorsal surface of the foot to the opposite, medial side of the foot where the second fastener member can there be attached to the first fastener member on that side of the foot. The same process is repeated in the opposite direction for the remaining medial strap section and fastener members.

The crossover strap, since it is preferably elastic, will allow for a significant amount of adjustment for different foot sizes. Furthermore, the substantial fastening surface areas of the first and second fastener members will facilitate such adjustment.

The support, when in place on the foot, is a very compact yet effective support structure. The first and second fastener members join to form a relatively thin sandwich arrangement due to the particular construction without overlap of the adjacent strap ends. Furthermore, the connected fastener members secure the straps at important areas to provide maximum support to underlying tissues.

It can be seen that application of the present support can be performed by a wearer with very little or no training. Ease of application will enable fast and effective application of ankle support even by untrained individuals.

In use, the crossover strap extends around and constricts the tarsus area of the foot, limiting inversion and eversion motions. This strengthens the foot against potential sprain. Additionally, the heel and plantar straps function to anchor the crossover strap ends and, themselves, function to compact the muscles, tendons, and ligaments interconnecting the various bony structures beneath, including the calcaneum 21, the talus 22, the navicular 23, and the cuneforms.

The compact condition of the present support when mounted to the wearer's ankle enables the wearer to use existing footwear without causing discomfort. A stocking can be applied over the support with comfort and the stockinged foot can be inserted into a typical shoe or other footwear without the difficulty experienced with many other forms of wraps or supports. This aids the comfort of the wearer and encourages use of the support.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. An ankle support, comprising:
    an elongated heel strap extending between a medial and a lateral end;
    an elongated plantar strap extending between a medial and a lateral end;
    first fastener members joining the respective like medial and lateral ends of the heel strap and plantar strap such that the medial ends of the heel and plantar straps are joined together and the lateral ends of the heel and plantar straps are likewise joined together and such that the heel strap can be received over the Achilles tendon area of the heel with its ends extending forwardly over medial and lateral sides of the foot and so the plantar strap can be received over the plantar surface of the foot adjacent the heel with the lateral and medial ends extending upwardly to lateral and medial surfaces of the foot;
    an elongated crossover strap extending between opposed free ends and fastened substantially midway between its free ends to the heel strap at a location thereon approximately midway between the medial and lateral heel strap ends, defining medial and lateral strap sections extending in opposite directions from the heel strap;
    second fastener members at the free ends of the crossover strap for releasable engagement with the first fastener members such that the medial crossover strap section can be extended diagonally over the foot to join the second fastener member thereon with the first fastener member at the lateral ends of the heel and plantar straps, and such that the lateral crossover strap section can be extended diagonally over the foot to join the second fastener member thereon with the first fastener member at the medial ends of the heel and plantar straps.

2. The ankle support of claim 1 further comprising a dorsal strap extending between medial and lateral ends joined to the first fastener members to form a foot receiving loop with the plantar strap.

3. The ankle support of claim 1 wherein the heel and plantar straps are formed of flexible fabric and wherein the first fastener members are formed of a fastener fabric and extend from the lateral and medial ends of the heel and plantar straps and the second fastener members are formed of a fastener fabric and extend from the free ends of the crossover strap.

4. The ankle support of claim 1 wherein the crossover and heel straps include width dimensions between upper and lower longitudinal edges and wherein the crossover strap is secured to the heel strap partially overlapping the upper edge of the heel strap such that the upper edge of the heel strap is situated between the upper and lower edges of the crossover strap.

5. The ankle support of claim 4 wherein the crossover and heel straps are connected by means such as stitching along a line perpendicular to the crossover and heel strap lengths.

6. The ankle support of claim 1 wherein the fastener members are formed of fabric hook-and-loop fastener sections.

7. An ankle support, comprising:
    heel lock means formed of a heel strap, a dorsal strap and a plantar strap, for being positioned on a wearer's foot with the heel strap extending forwardly along lateral and medial sides of the foot form the Achilles tendon area, and with the dorsal strap extending over the dorsal surface of the foot forwardly adjacent the ankle, and with the plantar strap extending transversely across the plantar surface of the foot adjacent the heel and upwardly along the lateral and medial foot surfaces to ends;
    an elongated crossover strap mounted approximately midway along its length to the heel lock with the crossover strap extending partially above the heel strap and having medial and lateral sections extending to free crossover strap ends on opposite sides of the heel lock, for connection in an operative condition to the heel lock, with said medial and lateral sections crossing over the dorsal surface of the foot and around the lower leg adjacent the ankle and elevationally above the plantar surface of the foot; and
    fastener means on the crossover strap and heel lock for releasably securing the strap ends with said crossover strap in its operative condition above the plantar surface of the foot.

8. The ankle support of claim 7 wherein:
    the dorsal strap includes medial and lateral ends extendable downwardly on opposite sides of the foot;
    the plantar strap includes medial and lateral ends extendible upwardly along medial and lateral surfaces of the foot;
    the heel strap includes medial and lateral ends extendible forwardly along lateral and medial surfaces of the foot; and
    wherein the fastener means includes first fastener members joining the medial ends of the heel, dorsal and plantar straps, and the lateral ends of the heel, dorsal, and plantar straps.

9. The ankle support of claim 7 wherein the fastener means includes second fastener members at the free elastic strap ends and first fastener members on the heel lock means for releasably securing the second fastener members.

10. An ankle support, comprising:
    an elongated elastic plantar strap having a length dimension between ends such that it can be extended transversely across the plantar surface of the wearer's foot and with ends extending upwardly along lateral and medial surfaces of the foot;
    an elongated elastic heel strap having a length dimension between ends such that it can be extended from the Archilles tendon area of the foot forwardly along lateral and medial sides thereof;

first fastener members joining the heel and plantar strap ends on the lateral and medial sides of the foot such that a heel lock is formed by the joined straps;

an elongated elastic crossover strap having a sufficient length dimension between free ends to be extended from the back surface of the foot adjacent the Achilles tendon, forwardly around the lower leg, and crossing over along the dorsal surface of the foot to the free ends; and second fastener members at the free ends of the crossover strap for releasably securing the free ends to the first fastener members.

11. The ankle support of claim 10 wherein the elongated elastic crossover strap is fastened at a location approximately midway along the crossover strap length to the heel strap at a location thereon approximately midway along the heel strap length.

12. The ankle support of claim 10 wherein the crossover and heel strap include width dimensions transverse lengths and wherein the crossover strap is attached to the heel strap with the width dimension of the crossover strap partially overlapping the width dimension of the heel strap.

13. The ankle support of claim 10 wherein the first and second fastener members are formed sections of fabric hook-and-loop fasteners and are attached to the ends of the straps.

14. The ankle support of claim 10 wherein the first and second fastener members are formed of fabric hook-and-loop fastener sections and wherein the first fasteners include edges sewn to the medial ends and lateral ends of the plantar and heel straps such that the first fastener sections extend from the plantar and heel strap ends.

15. The ankle support of claim 10 wherein the first fastener members include polygonal shaped medial and lateral fastener sections;
- wherein the medial fastener section includes a first edge joined to the medial end of the plantar strap and a second edge joined to the medial end of the heel strap; and
- wherein the lateral fastener section includes a first edge joined to the lateral end of the plantar strap and a second edge joined to the lateral end of the heel strap.

16. The ankle support of claim 15 wherein the first and second edge of each first fastener section are oriented at approximate right angles.

17. The ankle support of claim 10 further comprising a dorsal strap having a length dimension between ends such that it can be extended over the dorsal surface of the wearer's foot and with the ends thereof extending downwardly on opposite sides of the foot; and
- wherein the dorsal strap ends are attached to the first fastener members.

* * * * *